(12) United States Patent
Clarke et al.

(10) Patent No.: US 6,696,457 B1
(45) Date of Patent: Feb. 24, 2004

(54) MORPHINOID COMPOUNDS

(75) Inventors: Stephen Edward Clarke, Welwyn (GB); Giulio Dondio, Baranzate di Bollate (IT); Luca Francesco Raveglia, Baranzate di Bollate (IT); Silvano Ronzoni, Baranzate di Bollate (IT)

(73) Assignees: SmithKline Beecham p.l.c., Brentford Middlesex (GB); SmithKline Beecham S.p.A., Baranzate di Bollate (IT)

( * ) Notice: Subject to any disclaimer, the term of this patent is extended or adjusted under 35 U.S.C. 154(b) by 0 days.

(21) Appl. No.: 09/959,020

(22) PCT Filed: Apr. 20, 2000

(86) PCT No.: PCT/GB00/01516

§ 371 (c)(1),
(2), (4) Date: Apr. 2, 2002

(87) PCT Pub. No.: WO00/63210

PCT Pub. Date: Oct. 26, 2000

(30) Foreign Application Priority Data

Apr. 20, 1999 (IT) .......................... MI99A0816

(51) Int. Cl.$^7$ ...................... A61K 31/44; A61K 31/535; C07D 471/22; C07D 491/22

(52) U.S. Cl. ........................... 514/282; 546/44; 546/45; 546/46

(58) Field of Search ............................... 546/44, 45, 46; 514/282

(56) References Cited

U.S. PATENT DOCUMENTS 6,365,594 B1 * 4/2002 Dondio et al. .............. 514/279

FOREIGN PATENT DOCUMENTS

| WO | 96/02545 | * | 2/1996 |
| WO | wo 97 25331 | | 7/1997 |
| WO | 97/25331 | * | 7/1997 |

* cited by examiner

*Primary Examiner*—Rita Desai
(74) *Attorney, Agent, or Firm*—Soma G. Simon; Mary E. McCarthy; Charles M. Kinzig

(57) ABSTRACT

Heterocycle condensed morphinoid derivatives of formula (I) have therapeutic utility as analgesics, in collagen disease, as anti-allergic and anti-inflammatory agents, brain cell protectants, in gastritis, diarrhoea, cardiovascular and respiratory diseases, cough, mental illness, epilepsy, for the preservation of organs during transplant operations, and for the treatment of those pathological conditions which customarily can be treated with agonists of the delta opioid receptor.

5 Claims, No Drawings

MORPHINOID COMPOUNDS

The present invention is concerned with novel compounds, in particular novel morphinoid compounds, processes for their preparation and their use in medicine.

The presence of three populations of opioid receptors (mu, delta and kappa) is now well established and documented and all three are reported to be present in the central and peripheral nervous system of many species including man (Lord J. A. H. et al., *Nature* 1977, 267, 495).

Activation of all three opioid receptor subtypes can lead to antinociception in animal models. In particular, studies with peptidic delta agonists have indicated that activation of the delta receptor produces antinociception in rodents, primates and can induce clinical analgesia in man (D. E. Moulin et al. *Pain*, 1985, 23, 213). Evidence exists that suggest a lesser propensity of delta agonists to cause the usual side-effects associated with mu and kappa activation (Galligan et al, *J. Pharm. Exp. Ther.*, 1984, 229, 641).

U.S. Pat. No. 5,223,507 and U.S. Pat. No. 5,225,417 (G. D. Searle & Co.) disclose bicycle-condensed morphinoid compounds which are said to be delta opioid agonists having therapeutic utility as analgesics agents.

International Application Publication Number WO 94/07896 (Toray Ind. Inc.) discloses indole-condensed morphinoid compounds useful as immunosuppressants, anti-allergic and anti-inflammatory agents.

International Application Publication Numbers WO 96/02545 and WO 97/25331 (SmithKline Beecham S.p.A.) disclose a novel class of substituted monoheterocycle-condensed morphinoid derivatives which are stated to be potent and selective delta opioid agonists and antagonists. They are stated to have potential therapeutic utility as inter alia analgesics.

The contents of WO 96/02545 are incorporated herein by reference, including compounds of formula (IA) as defined below and the specific Examples disclosed therein:

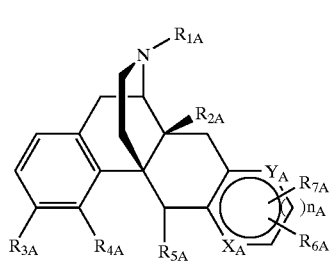

(IA)

wherein;
- $R_{1A}$ is hydrogen, linear or branched $C_{1-6}$ alkyl, $C_{3-7}$ cycloalkyl, $C_{4-6}$ cycloalkylalkyl, $C_{3-5}$ alkenyl, aryl, aralkyl or furan-2 or 3-yl alkyl or $(CH_2)_{m_A} COR_A$ wherein $m_A$ is 1 to 5 and $R_A$ represents hydroxy, $C_{1-5}$ alkoxy, $OC_{3-6}$ alkenyl or alkylaryl or $R_{1A}$ is a group $A_A-B_A$ wherein $A_A$ represents $C_{1-10}$ alkylene and $B_A$ represents substituted or unsubstituted aryl or heteroaryl;
- $R_{2A}$ is hydrogen, hydroxy or $C_{1-5}$ alkoxy, preferably methoxy, halogen, nitro, $NR_{8A}R_{9A}$, $SR_{8A}$, where $R_{8A}$ and $R_{9A}$, which may be the same or different, are each hydrogen, $C_{1-6}$ alkyl, $COR_{1A}$ preferably acetyl.
- $R_{3A}$ is hydrogen, hydroxy, $C_{1-5}$ alkoxy, preferably methoxy, halogen, $SR_{8A}$, preferably hydrogen, nitro, $NHR_{10A}$, $NR_{10A}R_{11A}$, $NHCOR_{10A}$, $NHSO_2R_{10A}$, where $R_{10A}$ and $R_{11A}$ which may be the same or different, are each hydrogen or $C_{1-6}$ alkyl, preferably methyl;
- $R_{4A}$ and $R_{5A}$, which may be the same or different, are each independently hydrogen, hydroxy, $C_{1-5}$ alkoxy, preferably methoxy, or together may form an oxy group (—O—);
- $R_{6A}$ is a group

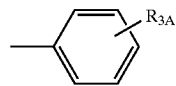

in which $R_{3A}$ has the same meaning described above, there being up to three $R_{3A}$ in the phenyl ring, or $R_{6A}$ is a group $C(Z_A)R_{12A}$, in which $Z_A$ is oxygen or sulphur, $R_{12A}$ is $C_{1-18}$ alkyl, $C_{1-18}$ alkoxy or $NR_{13A}R_{14A}$, where $R_{13A}$ and $R_{14A}$, which may be the same or different, are hydrogen, linear or branched $C_{1-6}$ alkyl, $C_{3-7}$ cycloalkyl, $C_{4-6}$ cycloalkylalkyl, $C_{3-6}$ alkenyl, aryl, aralkyl or an optionally substituted heterocyclic ring or may form together a $C_{3-6}$ alkyl ring which may be interrupted by an oxygen or a nitrogen.
- $R_{7A}$ is hydrogen, $C_{1-18}$ alkyl, $C_{2-18}$ alkenyl, or is a group

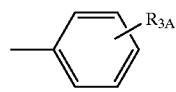

in which $R_{3A}$ has the same meaning described above;
- $n_A$ is 0 or 1;
- when $n_A=0$, then $X_A$ and $Y_A$ are independently NH, oxygen and sulphur or CH or a $R_{6A}$- or $R_{7A}$-substituted carbon atom; and when $n_A=1$, then $X_A$ and $Y_A$ are both N, or N and CH or a $R_{6A}$- or $R_{7A}$-substituted carbon atom.

The contents of WO 97/25331 are incorporated herein by reference, including compounds of formula (IB) as defined below and the specific Examples disclosed therein:

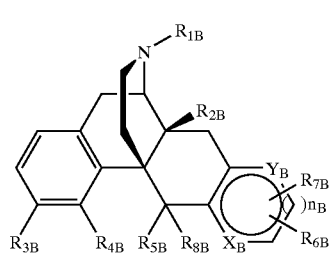

(IB)

wherein;
- $R_{1B}$ is hydrogen, linear or branched $C_{1-6}$ alkyl, $C_{3-7}$ cycloalkyl, $C_{4-6}$ cycloalkylalkyl, each of the latter three groups being optionally substituted by a hydroxy group when $C_{\geq 2}$, $C_{3-5}$ alkenyl, aryl, aralkyl or furan-2 or 3-yl alkyl or $(CH_2)m_BCOR_B$ wherein $m_B$ is 0 to 5 and $R_B$ represents linear or branched $C_{1-6}$ alkyl, hydroxy, $C_{1-5}$ alkoxy, $OC_{3-6}$ alkenyl or alkylaryl, $NR_{10B}R_{11B}$ where $R_{10B}$ and $R_{11B}$ may be the same or different, and each is hydrogen, linear or branched $C_{1-6}$ alky, $C_{4-6}$ cycloalkylalkyl, $C_{3-5}$ alkenyl, aryl or aralkyl; or $R_{1B}$ is a group $A_B-B_B$ wherein $A_B$ represents $C_{1-10}$ alkylene and $B_B$ represents substituted or unsubstituted aryl or heteroaryl;
- $R_{2B}$ is hydrogen, hydroxy or $C_{1-5}$ alkoxy, preferably methoxy, halogen, nitro, $NR_{10B}R_{11B}$, $SR_{10B}$, where $R_{10B}$ and $R_{11B}$ have the same meaning described above and in addition $R_{10B}$ is $COR_{1B}$, preferably acetyl;

$R_{3B}$ is hydrogen, linear or branched $C_{1-6}$ alkyl, preferably ethyl, hydroxy, $C_{1-5}$ alkoxy, preferably methoxy, halogen, preferably bromine, or $(CH_2)_{m_B}COR_B$ where $m_B$ and $R_B$ have the same meaning described above, $SR_{10B}$, nitro, $NR_{10B}R_{11B}$, $NHCOR_{10B}$, $NHSO_2R_{10B}$, where $R_{10B}$ and $R_{11B}$, have the same meaning described above, preferably hydrogen or methyl;

$R_{4B}$ and $R_{5B}$, which may be the same or different, are each independently hydrogen, hydroxy, $C_{1-5}$ alkoxy, preferably methoxy, O-phenyl or together may form an oxy group (—O—); or $R_{4B}$ together with $R_{3B}$ may form a methylendioxy group (—OCH$_2$O—);

$R_{6B}$ is a group

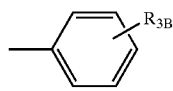

or a five- or six-membered heteroaromatic group, containing up to three heteroatoms such as O, S and N, substituted with $R_{3B}$ in which $R_{3B}$ has the same meaning described above, there being up to three $R_{3B}$ groups in the ring, or $R_{6B}$ is a group $C(Z_B)R_{12B}$, in which $Z_B$ is oxygen or sulphur, $R_{12B}$ is linear or branched $C_{1-18}$ alkyl, hydroxy, linear or branched $C_{1-18}$ alkoxy, aralkyloxy or $NR_{13B}R_{14B}$, where $R_{13B}$ and $R_{14B}$, which may be the same or different, are hydrogen, linear or branched $C_{1-6}$ alkyl, $C_{3-7}$ cycloalkyl, $C_{4-6}$ cycloalkylalkyl, each of the latter three groups being optionally substituted by up to three fluorine atoms or hydroxy group when $C_{\geq 2}$, $C_{3-6}$ alkenyl, aryl, aralkyl or an optionally substituted heterocyclic ring or $R_{13B}$ and $R_{14B}$ may form together a $C_{3-6}$ alkyl ring which may be interrupted by an oxygen or a $NR_{1B}$ where $R_{1B}$ has the same meaning described above, or $R_{6B}$ is a $CH_2W_BD_B$ group, where $W_B$ is oxygen, sulphur or $NR_{14B}$, and $D_B$ is hydrogen, linear or branched alkyl or $COR_{14B}$, where $R_{14B}$ is defined above and is preferably methyl;

or $R_{6B}$ is a $COCOR_{12B}$ group, where $R_{12B}$ has the same meaning described above, and is preferably $C_{1-18}$ alkoxy;

or $R_{6B}$ is a $NR_{13B}R_{14B}$ group, where $R_{13B}$ and $R_{14B}$ have the same meaning described above, or $R_{13B}$ may be a $(CH_2)_{m_B}COR_B$ group where $m_B$ and $R_B$ have the same meanings defined above;

or $R_{6B}$ is a $P(Z_B)R_{12B}$ group where $Z_B$ and $R_{12B}$ have the same meaning described above, and preferably $Z_B$=O and $R_{12B}$=$C_{1-18}$ alkoxy;

or $R_{6B}$ is a $S(O)_iR_{12B}$ group where i=1,2 and $R_{12B}$ has the same meaning described above;

$R_{7B}$ is hydrogen, $C_{1-18}$ alkyl, $C_{2-18}$ alkenyl, halogen, halogen-$C_{1-6}$ alkyl, $(CH_2)_{m_B}COR_B$ where $m_B$ and $R_B$ have the same meanings defined above or is a group

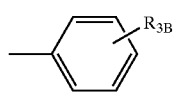

or a five- or six-membered heteroaromatic group, containing up to three heteroatoms such as O, S and N, substituted with $R_{3B}$ in which $R_{3B}$ has the same meaning described above;

$R_{8B}$ is hydrogen, $C_{1-6}$ alkyl preferably methyl;

$n_B$ is 0 or 1;

when $n_B$=0, then $X_B$ and $Y_B$ are independently oxygen, sulphur, CH or a $R_{6B}$- or $R_{7B}$-substituted carbon atom, and $NR_{9B}$, where $R_{9B}$ is hydrogen, linear or branched $C_{1-6}$ alkyl, $C_{3-7}$ cycloalkyl, $C_{4-6}$ cycloalkylalkyl, each of the latter three groups being optionally substituted by a hydroxy group when $C_{\geq 2}$, or may contain a $NR_{10B}R_{11B}$ group where $R_{10B}$ and $R_{11B}$ have the same meaning described above, $C_{3-5}$ alkenyl, aryl, aralkyl or $(CH_2)_{m_B}COR_B$ wherein $m_B$ is 0 to 5 and $R_B$ represents hydroxy, $C_{1-5}$ alkoxy, $OC_{3-6}$ alkenyl or alkylaryl, $NR_{10B}R_{11B}$ where $R_{10B}$ and $R_{11B}$ may be the same or different, are each hydrogen, linear or branched $C_{1-6}$ alkyl, $C_{4-6}$ cycloalkylalkyl; and when $n_B$=1, then $X_B$ and $Y_B$ are both N, or N and CH.

It has now surprisingly been discovered that certain novel compounds, some of which fall within the generic scopes of WO 96/02545 and WO 97/25531 have no delta opioid antagonist activity but are potent and selective delta opioid agonists and may therefore have potential therapeutic utility as analgesics, in collagen disease, as anti-allergic and anti-inflammatory agents, brain cell protectants, in gastritis, diarrhoea, cardiovascular and respiratory diseases, cough, mental illness, epilepsy, for the preservation of organs during transplant operations, and for the treatment of those pathological conditions which customarily can be treated with agonists of the delta opioid receptor. It has also surprisingly been found that certain of these compounds possess especially superior metabolic stability and hence they are considered to be of particular use as therapeutic agents.

Accordingly, in a first aspect the present invention, provides a compound of formula (I)

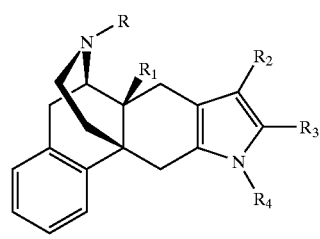

(I)

or a derivative thereof,
wherein;

R is hydrogen or methyl;

$R_1$ is hydrogen, hydroxy or $C_{1-5}$alkoxy;

$R_2$ is $C_{1-6}$alkyl;

$R_3$ is a group $C(O)R_7$, in which $R_7$ is iso-propyl, iso-butyl, ethoxy, iso-butoxy, or $NR_8R_9$, where $R_8$ and $R_9$ are each independently hydrogen, ethyl, iso-propyl, iso-butyl, cyclohexyl, phenyl, benzyl, o-pyridylmethyl, 2,6-dimethylpiperidyl, 2,5-dimethylpiperazyl, 2-(1-phenylbutyl), (4fluorophenyl)methyl, (3-fluorophenyl) methyl, (4-bromophenyl)methyl, (4-trifluoromethylphenyl)methyl, (4-isopropylphenyl) methyl, or $R_8$ and $R_9$ together form a $C_5$ aromatic ring, which ring is fused at the 3 and 4 positions to a phenyl ring to form a 2-isoquinolinyl ring, and;

$R_4$ is hydrogen or $C_{1-6}$alkyl.

Suitably, $R_1$ is hydrogen, hydroxy or methoxy.

Preferably, $R_2$ is methyl.

Suitably, $R_4$ is hydrogen or methyl.

Hence, the present invention also provides a group of compounds falling wholly within formula (I) being of formula (I')

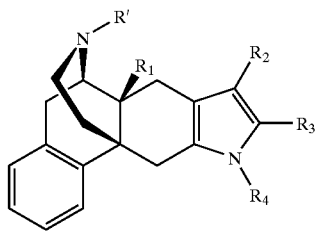

(I')

or a derivative thereof,
wherein;
R' is hydrogen;
$R_1$ is hydrogen, hydroxy or methoxy;
$R_2$ is methyl;
$R_3$ is a group $C(O)R_7$, in which $R_7$ is iso-propyl, iso-butyl, ethoxy, iso-butoxy, or $NR_8R_9$, where $R_8$ and $R_9$ are each independently hydrogen, ethyl, iso-propyl, iso-butyl, cyclohexyl, phenyl, benzyl, o-pyridylmethyl, 2,6dimethylpiperidyl, 2,5-dimethylpiperazyl, 2-(1-phenylbutyl), (4-fluorophenyl)methyl, (3-fluorophenyl)methyl, (4-bromophenyl)methyl, (4-trifluoromethylphenyl)methyl, (4-isopropylphenyl)methyl, or $R_8$ and $R_9$ together form a $C_5$ aromatic ring, which ring is fused at the 3 and 4 positions to a phenyl ring to form a 2-isoquinolinyl ring, and;
$R_4$ is hydrogen or methyl.

According to a further aspect of the present invention, there is provided a compound of formula (I') or a derivative thereof,
wherein;
R' is hydrogen;
$R_1$ is hydrogen, hydroxy or methoxy;
$R_2$ is methyl;
$R_3$ is a group $C(O)R_7$;
$R_7$ is iso-propyl, iso-butyl, ethoxy, iso-butoxy, or $NR_8R_9$, where $R_8$ and $R_9$, are each independently hydrogen, ethyl, iso-propyl, iso-butyl, cyclohexyl, phenyl, benzyl, o-pyridylmethyl, 2,6-dimethylpiperidyl, 2,5-dimethylpiperazyl, 2-(1-phenylbutyl), (4-fluorophenyl)methyl, (3-fluorophenyl)methyl, (4-bromophenyl)methyl, (4-trifluoromethylphenyl)methyl, or (4isopropylphenyl)methyl, and;
$R_A$ is hydrogen or methyl.

According to a further aspect of the invention, there is provided a compound of formula (I') or a derivative thereof, wherein;
R' is hydrogen;
$R_1$ is hydroxy;
$R_2$ is methyl;
$R_3$ is a group $C(O)R_7$;
$R_7$ is $NR_8R_9$ where $R_8$ and $R_9$ together form a $C_5$ aromatic ring, which ring is fused at the 3 and 4 positions to a phenyl ring to form a 2-isoquinolinyl ring, and;
$R_4$ is hydrogen.

Preferably, R' is hydrogen, $R_1$ is hydroxy, $R_2$ is methyl, $R_3$ is $C(O)N(iPr)CH_2Ph$, and $R_4$ is hydrogen.

Hence, the present invention further provides a group of compounds falling wholly within formula (I) being of formula (I")

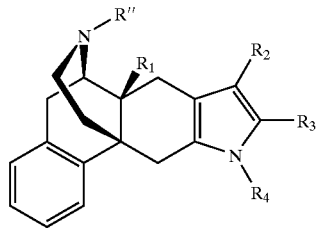

(I")

or a derivative thereof,
wherein;
R" is methyl;
$R_1$ is hydrogen, hydroxy or methoxy;
$R_2$ is methyl;
$R_3$ is a group $C(O)R_7$, in which $R_7$ is iso-propyl, iso-butyl, ethoxy, iso-butoxy, or $NR_8R_9$, where $R_8$ and $R_9$ are each independently hydrogen, ethyl, iso-propyl, iso-butyl, cyclohexyl, phenyl, benzyl, o-pyridylmethyl, 2,6-dimethylpiperidyl, 2,5-dimethylpiperazyl, 2-(1-phenylbutyl), (4-fluorophenyl)methyl, (3-fluorophenyl)methyl, (4-bromophenyl)methyl, (4-trifluoromethylphenyl)methyl, (4-isopropylphenyl) methyl, or $R_8$ and $R_9$ together form a $C_5$ aromatic ring, which ring is fused at the 3 and 4 positions to a phenyl ring to form a 2-isoquinolinyl ring, and;
$R_4$ is hydrogen or $C_{1-6}$alkyl.
Preferably, $R_4$ is methyl.

According to a further aspect of the present invention, there is provided a compound of formula (I") or a derivative thereof,
wherein;
R" is methyl;
$R_1$ is hydrogen, hydroxy or methoxy;
$R_2$ is methyl;
$R_3$ is a group $C(O)R_7$, in which $R_7$ is iso-propyl, iso-butyl, ethoxy, iso-butoxy, or $NR_8R_9$, where $R_8$ and $R_9$, are each independently hydrogen, ethyl, iso-propyl, iso-butyl, cyclohexyl, phenyl, benzyl, o-pyridylmethyl, 2,6-dimethylpiperidyl, 2,5-dimethylpiperazyl, 2-(1-phenylbutyl), (4-fluorophenyl)methyl, (3-fluorophenyl)methyl, (4-bromophenyl)methyl, (4-trifluoromethylphenyl)methyl, or (4-isopropylphenyl)methyl, and;
$R_4$ is hydrogen or methyl.

According to a further aspect of the invention, there is provided a compound of formula (I") or a derivative thereof, wherein;
R" is methyl;
$R_1$ is hydroxy;
$R_2$ is methyl;
$R_3$ is a group $C(O)R_7$;
$R_7$ is $NR_8R_9$ wherein $R_8$ and $R_9$ together form a $C_5$ aromatic ring, which ring is fused at the 3 and 4 positions to a phenyl ring to form a 2-isoquinolinyl ring, and;
$R_4$ is hydrogen.

Preferably, R" is methyl, $R_1$ is hydroxy, $R_2$ is methyl, $R_3$ is $C(O)N(iPr)CH_2Ph$, and $R_4$ is hydrogen.

Suitable derivatives of the compounds of the invention are pharmaceutically acceptable derivatives.

Suitable derivatives of the compounds of the invention include salts and solvates.

Suitable pharmaceutically acceptable derivatives include pharmaceutically acceptable salts and pharmaceutically acceptable solvates.

Suitable pharmaceutically acceptable salts include metal salts, such as for example aluminium, alkali metal salts such as lithium, sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)amine or tri-(2-hydroxyethyl)amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine, quinine or quinoline.

Suitable pharmaceutically acceptable salts also includes pharmaceutically acceptable acid addition salts, such as those provided by pharmaceutically acceptable inorganic acids or organic acids.

Suitable pharmaceutically acceptable acid addition salts provided by pharmaceutically acceptable inorganic acids includes the sulphate, nitrate, phosphate, borate, hydrochloride hydrobromide and hydroiodide.

Suitable pharmaceutically acceptable acid addition salts provided by pharmaceutically acceptable organic acids includes the acetate, tartrate, maleate, fumarate, malonate, citrate, succinate, lactate, oxalate, benzoate, ascorbate, methanesulphonate, α-keto glutarate and α-glycerophosphate, acetate, fumarate, salicylate, mandelate, and methanesulphonate.

Suitable pharmaceutically acceptable solvates include hydrates.

The compounds of formula (I) or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in a pharmaceutical composition. In the case of salts and solvates the additional ionic and solvent moieties must also be non-toxic.

The compounds of formula (I) may contain chiral atoms and/or multiple bonds and hence may exists in one or more stereoisomeric forms. The present invention extends to all such forms as well as to their mixtures thereof, including enantiomers, diatstereoisomers, geometric isomers, and racemic modifications.

Unless otherwise stated, alkyl groups referred to herein, including those forming part of other groups, include straight or branched chain alkyl groups containing up to twelve, suitably up to six carbon atoms. These alkyl groups may be optionally substituted with up to five, suitably up to three, groups selected from the list consisting of alkoxy, amino, carboxy and esters thereof, cyano, hydroxy, and halogen.

Unless otherwise stated, alkenyl and akynyl groups referred to herein include straight and branched chain groups containing from two to twelve, suitably from two to six, carbon atoms. These alkenyl and alkynyl groups may be optionally substituted with up to five, suitably up to three, groups including those substituents described hereinbefore for the alkyl groups.

WO 97125331 discloses general processes for the synthesis of compounds of formula (I) wherein R is hydrogen. Compounds of formula (I) wherein R is hydrogen may also be prepared from compounds of formula (I) wherein R is methyl.

Accordingly, the invention also provides a process for the preparation of compounds of formula (I) wherein R is hydrogen which process comprises demethylation of the piperidyl nitrogen atom of a compound of formula (I) wherein R is methyl.

In general, the compound of formula (I) wherein R is methyl is converted to its corresponding formate by reaction at a suitable initial temperature with a suitable chloroformate in a suitable solvent in the presence of a suitable proton removal medium and then heated to a suitable elevated temperature over a suitable reaction time under an inert atmosphere. A suitable initial temperature is 0–5° C. Suitable chloroformates are vinyl chloroformate and trichloroethyl chloroformate. Suitable solvents are dichloroethane and chloroform. Suitable proton removal media are a proton sponge or a base such as potassium bicarbonate. A suitable elevated temperature is the reflux temperature of the solvent. Suitable reaction times are those in the range 3–8 hours. A suitable inert atmosphere is a nitrogen atmosphere. The formate derivative is isolated by conventional means such as evaporation of the solvent, dissolution, washing, and reextraction followed by solvent removal to yield the desired formate derivative. The crude formate derivative is then converted into the compound of formula (I) wherein R is hydrogen by heating in a suitable solvent in the presence of a suitable acidic medium at a suitable temperature over a suitable period of time. Suitable solvents include ethanol and methanol. Suitable acidic media include hydrochloric acid and ammonium chloride in the presence of zinc. Suitable temperatures include the reflux temperature of the solvent. Suitable reaction times include those in the range 1–5 hours. The demethylated product is isolated by conventional means such as filtration, solvent removal by evaporation, dissolution, and reextraction followed by solvent removal. The crude product may be purified by conventional means such as chromatography. Conventional methods of heating and cooling, such as ice/salt baths and electric heating mantles may be employed.

In-a preferred aspect, a solution of the compound of formula (I) wherein R is methyl in 1,2-dichloroethane is added at 0° C. and under a nitrogen atmosphere to a solution of vinyl chloroformate and proton sponge in 1,2-dichloroethane. When the addition is complete the reaction mixture is refluxed for 6 hours, then the solvent is removed in vacuo. The residue is taken up in water, acidified, and extracted with diethyl ether. The organic phase is dried over $Na_2SO_4$ and the solvent is removed in vacuo. The resulting crude product is dissolved in ethanol containing 37% HCl and the reaction mixture is refluxed for 3 hours. The solvent is removed in vacuo, the residue taken up in water and extracted with diethyl ether. The aqueous phase is basified and extracted with dichioromethane. The organic phase is dried and the solvent removed in vacuo. The crude compound of formula (I) wherein R is hydrogen is then purified by flash chromatography.

In a further preferred aspect, the compound of formula (I) wherein R is methyl is dissolved chloroform, and potassium bicarbonate and trichloroethylchlorofomate added. The reaction mixture is refluxed for 4 hours and then cooled to room temperature. The solid is filtered and the organc solvent removed in vacuo. The residue is dissolved in methanol and ammonium chloride added. The reaction mixture is refluxed, zinc added portionwise, and the reflux continued for 3 hours. After cooling, the solid is removed by filtration and the organic solvent removed in vacuo. The residue is taken up with ammonium hydroxide solution and extracted with ethyl acetate. The organic phase is then dried and the solvent removed in vacuo. The crude compound of formula (I) wherein R is hydrogen is then purified by flash chromatography.

Alternatively, the compound of formula (I) wherein R is methyl is converted to its corresponding N-oxide by reaction with a oxidising agent in a suitable solvent at a suitable temperature over a suitable reaction time under a suitable inert atmosphere. A suitable oxidising agent in meta-chloroperoxybenzoic acid (MCPBA). A suitable solvent is dichloromethane. Suitable temperatures include those in the range 0–25° C. Suitable reacion times include those in the range of 1–3 hours. A suitable inert atmosphere is a nitrogen atmosphere. The N-oxide is isolated by conventional means such as washing with aqueous base, extraction with an organic solvent drying, and removal of the solvent by evaporation. The N-oxide is used without further purification. The N-oxide is reduced in a suitable solvent in the presence of a suitable reducing agent at a suitable temperature over a suitable period of time. Suitable solvents include dichloromethane. Suitable reducing agents include iron (II) chloride. Suitable temperatures include those in the range 0–25° C. Suitable reaction times include those in the range of 1–6 hours. The desired compound of formula (I) wherein R is hydrogen is isolated by conventional means such as basification, extraction, drying and removal of the solvent by evaporation. The product may be purified using conventional techniques such as chromatography and trituration. Conventional methods of heating and cooling, such as ice/salt baths and electric heating mantles may be employed.

In a preferred aspect, the compound of formula (I) wherein R is methyl is dissolved in anhydrous dichloromethane under a nitrogen atmosphere at 5° C. with stirring. m-Chloroperbenzoic acid is added portionwise over 30 minutes and stirring continued for an additional 30 minutes. The mixture is allowed to reach ambient temperature and held at this temperature for two hours. The reaction mixture is then washed with potassium carbonate, and extracted twice with dichloromethane. The organic phase is dried and the solvent removed in vacuo to yield the corresponding N-oxide. The N-oxide is dissolved in dichloromethane. To this solution, a solution of iron (II) chloride in water is added dropwise maintaining a temperature of 0° C. for one hour. The reaction mixture is allowed to reach ambient temperature and maintained at this temperature with stirring for further 4 hours the solvent removed in vacuo. The residue is taken up in diethyl ether, ethylenediamine added, followed by sodium hydroxide solution.

The aqueous layer is extracted twice with diethyl ether, the organic layers combined, dried, and the solvent removed in vacuo. The resulting residue is purified by flash chromatography. The pure compound of formula (I) wherein R is hydrogen is then triturated with boiling diisopropyl ether.

A further aspect of the invention provides a process for the preparation of a compound of formula (I) wherein R is methyl and $R_4$ is hydrogen which process comprises the reaction of a compound of formula (III)

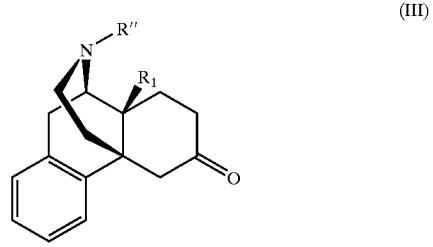

(III)

wherein;
R" is as defined in formula (I") and $R_1$ is as defined in formula (I), with a compound of formula (IV)

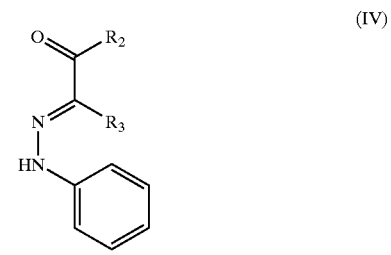

(IV)

wherein;
$R_2$ and $R_3$ are as defined in formula (I), in the presence of zinc and sodium acetate in acetic acid as generally described in Khimiya Geterot. Soed. 342 (1972), and thereafter, if required, carrying out one or more of the following optional steps:
(i) converting a compound of formula (I) wherein R is methyl to another compound of formula (I) wherein R is methyl;
(ii) removing any necessary protecting group;
(iii) preparing an appropriate derivative of the compound so formed.

In general, a solution of the compound of formula (III), the compound of formula (IV), and a suitable base in a suitable solvent is heated to a suitable temperature. A suitable base is sodium acetate. A suitable solvent is acetic acid. A suitable temperature is in the range 60–100° C. Zinc powder is added and the mixture heated at a higher temperature, in the range 90–130° C. for a suitable period of time. A suitable period of time is 2–5 hours. The mixture is then poured onto ice, basified, and extracted with a suitable organic solvent. A suitable organic solvent is ethyl acetate. The organic layer is extracted with a suitable aqueous mineral acid, for example dilute hydrochloric acid, the aqueous layer isolated, basified with, for example, ammonium hydroxide, and extracted with a suitable organic solvent, for example dichloromethane. The organic layer is dried and the solvent removed by evaporation. The crude product is then purified by conventional means, such as flash chromatography and crystallisation. Conventional methods of heating, such as electric heating mantles may be employed.

In a preferred aspect, the compound of formula (III), the compound of formula (IV), and sodium acetate are dissolved in acetic acid and the solution heated to 80° C. Zn powder is added portionwise and the reaction mixture heated at 110° C. for 3.5 hours. The mixture is then poured into ice, basified with ammonium hydroxide and extracted with ethyl acetate.

The organic layer is extracted with dilute hydrochloric acid, the aqueous layer separated, basified with ammonium hydroxide, and extracted with dichloromethane. The organic layer is dried over magnesium sulphate, filtered and evaporated to dryness. The crude product thus obtained is purified by flash chromatography and then crystallised.

Compounds of formula (III) are described in *Helv. Chim. Acta* 65 2394–2404(1982).

Compounds of formula (IV) are described in *Organic Reactions* 103–142 (1959).

The above mentioned conversion of a compound of formula (I) wherein R is methyl into another compound of formula (I) wherein R is methyl includes any conversion which may be effected using conventional procedures, but in particular the said conversions include converting one group $R_4$ into another group $R_4$. This conversion may be carried out using any appropriate method under conditions determined by the particular groups chosen. A suitable conversion of one group $R_4$ into another group $R_4$ includes converting a group $R_4$ which represents hydrogen into a group $R_4$ which represents alkyl; such a conversion may be carried out using a conventional alkylation procedure for example treating an appropriately protected compound of formula (I) wherein R is methyl with a suitable alkylating agent such as an alkyl halide, for example a methyl halide, in the presence of suitable strong base such as sodium hydride.

The compounds of formula (I) may be converted into their pharmaceutically acceptable salts by reaction with the appropriate organic or mineral acids.

Solvates of the compounds of formula (I) may be formed by crystallization or recrystallization from the appropriate solvent. For example, hydrates may be formed by crystallization or recrystallization from aqueous solutions, or solutions in organic solvents containing water.

Salts or solvates of the compounds of formula (I) which are not pharmaceutically acceptable may be useful as intermediates in the production of pharmaceutically acceptable salts or solvates. Accordingly such salts or solvates also form part of this invention.

Compounds of formula (I) acting as selective delta receptor ligands may be useful as analgesics, immunosuppressants to prevent rejection in organ transplant and skin graft, anti-allergic and anti-inflammatory agents, brain cell protectant, for the treatment of drug and alcohol abuse, to decrease gastric secretion, for the treatment of diarrhoea, cardiovascular and respiratory diseases, cough and respiratory depression, mental illness, epileptic seizures and other neurologic disorders (herein after referred to as Conditions). In particular, the activity of the compounds of formula (I) as delta agonists in standard tests indicates that they are of potential therapeutic utility as analgesic agents for the amelioration or elimination of pain. Compounds of the present invention are also useful in those diseases in which alteration or dysfunction of the opioidergic network is present or in someway evident in the pathological condition.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of the Conditions.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known agents for treating the Conditions.

Preferably, a pharmaceutical composition of the invention is in unit dosage form and in a form adapted for use in the medical or veterinarial fields. For example, such preparations may be in a pack form accompanied by written or printed instructions for use as an agent in the treatment of the Conditions.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, antioxidants or other preservatives, buffers or solutes to render the solution isotonic with the blood, thickening agents, suspending agents or other pharmaceutically acceptable additives. Such forms will be presented in unit dose form such as ampoules or disposable injection devices or in multidose forms such as a bottle from which the appropriate dose may be withdrawn or a solid form or concentrate which can be used to prepare an injectable formulation.

The compounds of this invention may also be administered by inhalation, via the nasal or oral routes. Such administration can be carried out with a spray formulation comprising a compound of the invention and a suitable carrier, optionally suspended in, for example, a hydrocarbon propellant.

Preferred spray formulations comprise micronised compound particles in combination with a surfactant, solvent or a dispersing agent to prevent the sedimentation of suspended particles. Preferably, the compound particle size is from about 2 to 10 microns.

A further mode of administration of the compounds of the invention comprises transdermal delivery utilising a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber or silicone can be used.

As mentioned above, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose. No unacceptable toxicological effects are expected with compounds of the invention when administered in accordance with the invention.

The present invention also provides a method for the treatment and/or prophylaxis of the Conditions in mammals, particularly humans, which comprises administering to the mammal in need of such treatment and/or prophylaxis an effective amount of a compound of formula (I) or a pharmaceutically acceptable salt or solvate thereof.

It has further been determined that compounds of the present invention when isotopically labelled, for example with the isotope $^{11}$C, have application in techniques such as positron emission tomography (PET).

Accordingly, the present invention provides a compound of formula (I) when isotopically labelled. The present invention therefore also provides the use of isotopically labelled compounds of formula (I) as imaging and diagnostic tools in PET.

It has also been determined that compounds of formula (IA) and compounds of formula (IB) when isotopically labelled, for example with the isotope $^{11}$C, have application in techniques such as positron emission tomography (PET).

Accordingly, the present invention provides a compound of formula (IA) or formula (IB) when isotopically labelled. The present invention therefore also provides the use of isotopically labelled compounds of formula (IA) or formula (IB) as imaging and diagnostic tools in PET.

Pharmacological Data

The activity of the compounds of the present invention as selective delta ligands is determined in radioligand binding assays using cloned human delta, mu and kappa opioid receptors stably expressed in cell lines as described below. CHO cells were subjected to stable transfection with cDNA encoding the human delta and mu opioid receptors. Clones were grown in suspension culture in serum free media. Selection was performed by growth in the absence of nucleotides. Human kappa opioid receptors were stably expressed in HEK cells. Cells were grown in adhesion in E-MEM supplemented with 10% FBS and 2 mM L-glutamine, G418 was included for selection.

Membraries were prepared as previously described (*J. Med. Chem.* (1997), 40, 3192). The binding of the preferential delta ligand [$^3$H]-[D-Ala$^2$,D-Leu$^5$]-enkephalin (DADLE) was evaluated at its $K_D$ concentration (0.7nM). The binding of the mu ligand [$^3$H]-DAMGO (*Eur. J. Pharmacol.*, 1989, 166, 213) and of the kappa ligand [$^3$H]-U69593 (Excerpta Medica, 1990, 211) were carried out at 0.5 nM. Non specific binding was determined in the presence of 10 uM of naloxone. Binding data were expressed as percentage of inhibition and fitted the following equation: f(x)=100-X/(IC$_{50}$+X) where X is the cold drug concentration value. The IC$_{50}$ values obtained were used to calculate the inhibitory constants ($K_i$) accordingly to the Cheng and Prusoff relation (*Biochem. Pharmacol.*, 1973, 22, 3099).

The delta agonistlantagonist activity of the compounds of the present invention is determined in the cAMP bioassay in CHO cell lines stably expressing the human delta opioid receptor (h-DOR/CHO).

For the cAMP assay whole h-DOR/CHO cells were incubated with test compounds in Krebs-Ringer 200 mM, buffered with HEPES, containing (mM): NaCl (125), KCl (5), KH$_2$PO$_4$ (0.4), MgSO4 (1.2), CaCl$_2$ (1.2), NaHCO$_3$(25), glucos (12) and IBMX (1). Cells were treated with forskolin 10 mM to stimulate cAMP synthesis.

The cAMP content was determined using a double antibody [$^{125}$I]-cAMp radioimmunoassay (Amersham RPA 509). The data were normalised to protein content.

The most potent compounds described in the present invention showed affinities for the delta receptor ranging from 0.5 to 200 nM with delta selectivity ranging from 20 to 1500 times in respect to the other opioid receptor types. These compounds also displayed potent delta agonist properties in the cAMP inhibition bioassay. Selective delta agonists (antagonised by the selective delta antagonist naltrindole) displayed IC$_{50}$ values ranging from 0.05 to 500 nM. For example, the compound of Example 2 showed an agonist activity in the inhibition of forskolin-stimulated cAMP in h-DOR/CHO cells (IC$_{50}$=1.15 nM) completely antagonised by the selective delta antagonist naltrindole (100 nM).

The rat carrageenan plantar test (*Pain* 1988, 32, 77) and Seltzer test (*Pain* 1990, 43, 205) were adopted to evaluate the antinociceptive efficacy of the compounds of the present invention.

Table 1 shows the relative metabolic stability data for the compounds of formula (I') and their N-methyl analogues i.e. compounds of formula (I"). The metabolic stability of the compounds of the invention was determined in the following manner: the compounds were incubated (37° C.) at 0.5 uM over 30 minutes with microsomal protein (at a concentration of 0.5 mg/ml) and an NADPH regenerating system (cofactor); the incubation volume was made up to a total of 1 mL with 50 mM potassium phosphate buffer (pH 7.4).

All of the incubation components, apart from cofactor, were pre-incubated for approximately 5 minutes then the reaction was started by the addition of cofactor solution. 50 uL samples were removed from the incubation at 3 minute intervals and placed into 200 uL of acetonitrile (containing an Internal Standard) to precipitate the microsomal protein and terminate the reaction.

All samples were analysed by LC/MS for parent compound and Internal Standard (I.S) and the results calculated as peak area ratios: compound/I.S.

The peak area ratios were plotted against time and intrinsic clearance values were calculated from the fitted exponential decay curve:

CLint (mL/min/g liver)=(k·V·microsomal yield)/[protein]

where:

k=rate constant from the exponential decay curve
V=incubation volume (1 mL)
microsomal yield=standard microsomal protein yield from 1 g liver (52.5 mg)
[protein]=protein concentration in each incubation (0.5 mg/mL);
a solution containing 0.5 uM of the compound under study was incubated with 0.5 mg of liver microsomal protein over 30 min at 37° C. Samples were taken, protein precipitated with acetonitrile and centrifuged prior HPLC-MS analysis.

TABLE 1

| | in vitro | in vivo | |
|---|---|---|---|
| | Clearance (human microsomes) CL (ml/min/g liver) | Clearance CL (ml/min/kg) | Absolute bio-availability F ipv (%) |
| Example 1 | 1.3 | | |
| N-Methyl analogue | 5.7 | | |
| Example 3 | 0.8 | 27 ± 2 | 60 ± 7 |
| N-Methyl analogue* | 7.9 | 62 ± 11 | 29 ± 5 |
| Example 4 | 3.3 | | |
| N-Methyl analogue | 6.8 | | |
| Example 5 | 2.0 | | |
| N-Methyl analogue | 3.3 | | |
| Example 6 | <0.6 | | |
| N-Methyl analogue | 6.0 | | |
| Example 7 | <0.6 | | |
| N-Methyl analogue | 1.6 | | |
| Example 8 | 5.9 | | |
| N-Methyl analogue | 8.1 | | |
| Example 9 | 4.5 | | |
| N-Methyl analogue | 21.0 | | |
| Example 10 | 5.2 | | |
| N-Methyl analogue | 5.3 | | |
| Example 11 | 13.0 | | |
| N-Methyl analogue | 32.0 | | |

*Example 75 from WO 97/25531

As indicated above, certain of the compounds of the invention have superior metabolic stability. It may be seen from Table 1 that the compounds of the invention wherein R is hydrogen show lower clearance, i.e. superior metabolic stability than the corresponding compounds wherein R is methyl. In addition, the clearance in vivo of Example 3 is lower than that of its N-methyl analogue. The absolute bioavailability of Example 3 is also superior to that of its N-methyl analogue, indicating a low first pass metabolism.

The following Examples illustrate the invention, but do not limit it in any way:

EXAMPLE 1
[10R,4bR-(4b beta,9a beta)]-7-(N,N-diisopropyl) aminocarbonyl-8-methyl-4b,5,9,9a, 10,11-hexahydro-9a-hydroxy-(6H)-10,4b-(iminoethano)phenanthro[3,2-b]pyrrole

EXAMPLE 2
[10R,4bR-(4b beta,9a beta)]-7-[(N-benzyl-N-isopropyl) aminocarbonyl]-8-methyl-4b,5,9,9a, 10,11-hexahydro-9a-hydroxy-(6H)-10,4b-(iminoethano)phenanthro-[3,2-b]pyrrole

EXAMPLE 3
[10R,4bR-(4b beta,9a beta)]-7-(N,N-diethyl) aminocarbonyl-8-methyl-4b,5,9,9a, 10,11-hexahydro-9a-hydroxy-(6H)-10,4b-(iminoethano)phenanthro[3,2-b]pyrrole

EXAMPLE 4
[10R,4bS-(4b beta,9a beta)]-7-(N-isopropyl-N-benzyl) aminocarbonyl-8-methyl-4b,5,9,9a, 10,11-hexahydro-(6H)-10-,4b-(iminoethano)phenanthro[3,2-b]pyrrole

EXAMPLE 5
[10R,4bR-(4b beta,9a beta)]-7-(N-benzyl-N-ethyl) aminocarbonyl-8-methyl-4b,5,9,9a, 10,11-hexahydro-9a-hydroxy-(6H)-10,4b-(iminoethano)phenanthro[3,2-b]pyrrole

EXAMPLE 6
[10R,4bR-(4b beta,9a beta)]-7-( 1,2,3,4-tetrahydroisoquinolin-2-yl)carbonyl-8-methyl-4b,5,9,9a, 10,11-hexahydro-9a-hydroxy-(6H)-1 0,4b-(iminoethano) phenanthro[3,2-b]pyrrole

EXAMPLE 7
[10R,4bR-(4b beta,9a beta)]-7-isobutylcarbonyl-8-methyl4b,5,9,9a,10,11-hexahydro-9a-hydroxy-(6H)-10,4b-(iminoethano)phenanthro[3,2-b]pyrrole

EXAMPLE 8
[10R,4bR-(4b beta,9a beta)]-7-[(N-phenyl-N-ethyl) aminocarbonyl]-4b,5,9,9a, 10,11-hexahydro-9a-hydroxy-(6H)-8-methyl-10,4(iminoethano)-phenanthro[3,2-b]pyrrole

EXAMPLE 9
[10R,4bS-(4b beta,9a beta)]-7-(N-ethyl-N-phenyl) aminocarbonyl-8-methyl-4b,5,9,9a, 10,11-hexahydro-(6H)-10,4b-(iminoethano)phenanthro[3,2-b]pyrrole

EXAMPLE 10
[10R,4bS-(4b beta,9a beta)]-7-(N-benzyl-N-isopropyl) aminocarbonyl-6,8-dimethyl-4b,5,9,9a, 10,11-hexahydro-9a-hydroxy-(6H)-10,4b-(iminoethano)-phenanthro[3,2-b]pyrrole

EXAMPLE 11
[10R,4bS-(4b beta,9a beta)]-7-(N-ethyl-N-benzyl) aminocarbonyl-6,8-dimethyl-4b,5,9,9a,10,11-hexahydro-(6H)-10-,4b-(iminoethano)phenanthro[3,2-b]pyrrole

EXAMPLE 12
[10R,4bR-(4b beta,9a beta)]-7-N-(cis-2,6-dimethyl)piperidinylcarbonyl-4b,5,9,9a,10,11-hexahydro-9a-hydroxy-(6H)-8-methyl-10,4b-(iminoethano)-phenanthro[3,2-b]pyrrole

EXAMPLE 13
[10R,4bR-(4b beta,9a beta)]-7-[(N-benzyl-N-ethyl)aminocarbonyl]-4b,5,9,9a,10,11-hexahydro-9a-methoxy-(6H)-8-methyl-10,4b-(iminoethano)-phenanthro[3,2-b]pyrrole

EXAMPLE 14
[10R,4bR-(4b beta,9a beta)]-7-[(N-(4-trifluoromethyl)phenylmethyl-N-isopropyl)aminocarbonyl]4b,5,9,9a,10,11-hexahydro-9a-hydroxy-(6H)-8-methyl-10,4b-(iminoethano)-phenanthro[3,2-b]pyrrole.

EXAMPLE 15
[10R,4bR-(4b beta,9a beta)]-7-[(N-(3-fluoro)phenylmethyl-N-isopropyl)aminocarbonyl]-4b,5,9,9a,10,11-hexahydro-9a-hydroxy-(6H)-8-methyl-10,4b(iminoethano)-phenanthro[3,2-b]pyrrole

EXAMPLE 16
[10R,4bR-(4b beta,9a beta)]-7-[(N-(4-bromo)phenylmethyl-N-isopropyl) aminocarbonyl]-4b,5,9,9a,10,11-hexahydro-9a-hydroxy-(6H)-8-methyl-10,4b-(iminoethano)-phenanthro[3,2-b]pyrrole

EXAMPLE 17
[10R,4bR-(4b beta,9a beta)]-7-[(N-(4-isopropyl)phenylmethyl-N-isopropyl)aminocarbonyl]-4b,5,9,9a,10,11-hexahydro-9a-hydroxy-(6H)-8-methyl-10,4b-(iminoethano)-phenanthro[3,2-b]pyrrole

EXAMPLE 18
[10R,4bR-(4b beta,9a beta)]-7-[(N-benzyl-N-cyclohexyl)aminocarbonyl]-4b,5,9,9a,10,11-hexahydro-9a-hydroxy-(6H)-8-methyl-10,4b-(iminoethano)-phenanthro[3,2-b]pyrrole

EXAMPLE 19
[10R,4bR-(4bb,9ab)]-7-(N,N-diisopropyl)aminocarbonyl-8,14-dimethyl4b,5,9,9a,10,11-hexahydro9a-hydroxy-(6H)-10,4b-(iminoethano)phenanthro[3,2-b]pyrrole.

EXAMPLE 20
[10R,4bR-(4b beta,9a beta)]-7-(N-benzyl-N-isopropyl)aminocarbonyl-8,14-dimethyl-4b,5,9,9a,10,11-hexahydro-9a-hydroxy-(6H)-1 0,4b-(iminoethano)phenanthro[3,2-b]pyrrole

EXAMPLE 21
[10R,4bR-(4b beta,9a beta)]-7-(1,2,3,4-tetrahydroisoquinolin-2-yl)carbonyl-8,14-dimethyl-4b,5,9,9a,10,11-hexahydro-9a-hydroxy-(6H)-10,4b-(iminoethano)phenanthro-[3,2-b]pyrrole

Synthesis A
[10R,4bR-(4b beta,9a beta)]-7-(N,N-diisopropyl)aminocarbonyl-8-methyl-4b,5,9,9a,10,11-hexahydro-9a-hydroxy-(6H)-10,4b-(iminoethano)phenanthro[3,2-b]pyrrole (Example 1)

A solution of 0.73 g (1.7 mmol) of [10R,4bR-(4bb,9ab)]-7-(N,N-diisopropyl)aminocarbonyl-8,14-dimethyl-4b,5,9,9a, 10,11-hexahydro-9a-hydroxy-(6H)-10,4b-(iminoethano)phenanthro[3,2-b]pyrrole in 20 mL of 1,2-dichloroethane is added at 0° C. and under a nitrogen atmosphere to a solution of 0.43 mL (5.0 mmol) of vinyl chloroformate and 0.546 g (2.5 mmol) of proton sponge in 15 mL of 1,2-dichloroethane. When the addition is complete the reaction mixture is refluxed for 6 hours, then the solvent is removed in vacuo. The residue is taken up in water, brought to acidic pH with 1N HCl and extracted with $Et_2O$. The organic phase is dried over $Na_2SO_4$ and the solvent is removed in vacuo. The resulting crude product (0.6 g) is dissolved in 10 mL of EtOH containing 0.6 mL of 37% HCl and the reaction mixture refluxed for 3 hours, the solvent is removed in vacuo, and the residue is taken up in water and extracted with $Et_2O$. The aqueous phase is basified with 2N NaOH and extracted with $CH_2Cl_2$; the organic phase is dried and the solvent removed in vacuo. The crude product is purified by flash chromatography, eluting with a mixture $CH_2Cl_2$/MeOH/conc.$NH_4OH$ 79:15:1 respectively, yielding 0.21 g of an amorphous solid which is crystallised from acetone, yielding 0.11 g of the title compound.

Synthesis B
[10R,4bR-(4b beta,9a beta)]-7-[(N-benzyl-N-isopropyl)aminocarbonyl]-8-methyl-4b,5,9,9a,10,11-hexahydro-9a-hydroxy-(6H)-10,4b-(iminoethano)phenanthro-[3,2-b]pyrrole hydrochloride (Example 2).

22.2 g of [10R,4bR-(4b beta,9a beta)]-7-(N-benzyl-N-isopropyl)aminocarbonyl-8,14-dimethyl-4b,5,9,9a,10,11-hexahydro-9a-hydroxy-(6H)-10,4b-(iminoethano)phenanthro[3,2-b]pyrrole (0.046 mol) were dissolved in 480 ml of $CHCl_3$ and 152 g (1.52 mol) of $KHCO_3$ and 63.3 ml (0.46 mol) of trichloroethylchlorofomate added. The reaction mixture was refluxed for 4 hours and then cooled to room temperature. The solid was filtered and the organc solvent was removed in vacuo. The resulting residue was dissolved in 600 ml of MeOH and 59 g (1.10 mol) of $NH_4Cl$ was added. The reaction mixture was heated to reflux, 60 g (0.92 mol) of Zn was added portionwise, and the reflux continued for 3 hours. After cooling, the solid was removed by filtration and the organic solvent removed in vacuo. The residue was taken up with $NH_4OH$ 15% and extracted with ethyl acetate. The organic phase was dried over $Na_2SO_4$ and the solvent removed in vacuo. The crude residue was purified by flash chromatography, eluting by $CH_2Cl_2$/MeOH/conc. $NH_4OH$ from 95:5:0.5 to 80:20:0.5, yielding 13 g (0.027 mol) of product. The product was dissolved in 200 ml of MeOH and cooled at 0° C. and a solution of HCl/$Et_2O$ 20% was added dropwise until pH=5. The mixture was allowed to warm to room temperature, and the solvent removed in vacuo. The residue was boiled in 100 ml of absolute EtOH for 1 hour. After cooling, the product was filtered, washed with absolute EtOH and dried yielding 9.1 (0.018 mol) g of the title compound.

Synthesis C
[10R,4bR-(4b beta,9a beta)]-7-(1,2,3,4-tetrahydroisoquinolin-2-yl)carbonyl-8-methyl4b,5,9,9a,10,11-hexahydro-9a-hydroxy-(6H)-10,4b-(iminoethano)phenanthro-[3,2-b]pyrrole (Example 6).

0.435 g of [10R,4bR-(4b beta,9a beta)]-7-(1,2,3,4-tetrahydroisoquinolin-2-yl)carbonyl-8,14-dimethyl4b,5,9,9a,10,11-hexahydro-9a-hydroxy-(6H)-10,4b-(iminoethano)phenanthro-[3,2-b]pyrrole (0.93 mmol) were dissolved in 2 ml of anhydrous dichloromethane. Under a nitrogen atmosphere and at 5° C., 0.21 g (0.97 mmol) of m-chloroperbenzoic acid were added portionwise over 30 min. Stirring was continued for additional 30 min at 5° C. The mixture was allowed to reach ambient temperature and held at this temperature for 120 min. The reaction mixture was then washed with 10% $K_2CO_3$ and extracted twice with dichloromethane. The organic phase was dried over $Na_2SO_4$ and the solvent removed in vacuo to yield 0.37 g of the corresponding N-oxide. The N-oxide was dissolved in 10 ml of dichloromethane. To the resulting solution, 0.6 mL of 1M $FeCl_2$ in water were added dropwise maintaining a temperature of 0° C. for 60 min. The reaction mixture was allowed to reach ambient temperature and maintained at this temperature with stirring for further 4 hours then the solvent was removed in vacuo. The residue was taken up in diethyl ether, 0.7 mL of ethylenediamine was added followed by 10 ml of 2.5 N NaOH. The aqueous layer was extracted twice with diethyl ether, the organic layers combined, dried over $Na_2SO_4$ and the solvent removed in vacuo. The resulting residue was purified by flash chromatography, eluting by $CH_2Cl_2$/MeOH/conc. $NH_4OH$ from 86:10:0.6 to 80:20:1, yielding 0.2 g of the title compound (yield 46%). The pure compound was then triturated with boiling diisopropyl ether.

Synthesis D

[10R,4bR-(4b beta,9a beta)]-7-(N-benzyl-N-isopropyl)aminocarbonyl-8,14-dimethyl-4b,5,9,9a,10,11-hexahydro-9a-hydroxy-(6H)-10,4b-(iminoethano)phenanthro[3,2-b]pyrrole (Example 20)

14-Hydroxy-17-methylmorphinan-6-one (10 g, 36.9 mmol), N-benzyl-N-isopropyl-2-phenylhydrazono-3-oxobutyramide (37.2 g, 110.7 mmol), AcONa (9.1 g, 110.7 mmol) were dissolved in AcOH (200 mL) and the solution was heated to 80° C. Zn powder (14.5 g, 221.4 mmol) was added portionwise and then the reaction mixture was heated at 110° C. for 3.5 hours. The mixture was then poured into ice, basified with 30% $NH_4OH$ and extracted with EtOAc. The organic layer was extracted with 5% HCl; the aqueous layer was separated, basified with 30% $NH_4OH$ and extracted with $CH_2Cl_2$. The organic layer was dried over $MgSO_4$, filtered and evaporated to dryness. The crude material thus obtained was purified by flash column chromatography on 230–400 mesh silica gel, utilising as eluent a mixture of $CH_2Cl_2$/MeOH/30% $NH_4OH$ 94:4:0.5 and then was crystallised from i-$Pr_2O$/acetone to yield 11.5 g of the title compound as a white solid.

TABLE 2

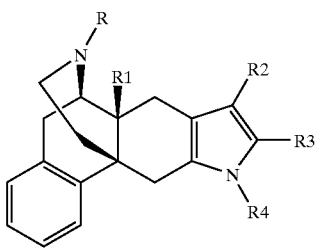

| Ex. | R | R1 | R2 | R3 | R4 | Synthesis | MP (° C.) (crystallization solvent) | MS m/z | MS conditions | NMR (δ ppm) |
|---|---|---|---|---|---|---|---|---|---|---|
| 1 | H | OH | Me | CON(iPr)$_2$ | H | A | 155–160 (free base, acetone) | A) 422 (MH+) B) 322; 304; 275; 168 | A) ESI POS; TSQ 700; MeOH/spray 4.5 kV/skimmer: 60 V/capillary 220 C B) ESI DAU + 422 (Collision gas: Argon) | (CDCl3): 8.20(s br, 1H); 7.20(m, 1H); 7.09(m, 3H); 3.92–3.82(m, 2H); 3.50(dd, 1H); 3.28(d br, 1H); 3.15(d, 1H); 3.15(d, 1H); 2.89(d, 1H); 2.70(m, 2H); 2.41(d, 1H); 2.31(d, 1H); 2.22–2.12(m, 1H); 1.80(s, 3H); 1.70(s br, 2H); 1.30(d, 12H); 1.25(m, 1H). |
| 2 | H | OH | Me | CON(iPr)CH$_2$Ph | H | B | >250 (.HCl, EtOH) | 470 (MH+) | ESI POS; TSQ 700; MeOH/spray 4.5 kV/skimmer: 60 V/capillary 220 C | (CDCl3): 8.38(s br, 1H); 7.25–7.12(m, 6H); 7.08(m, 3H); 4.69(d, 1H); 4.42(d, 1H); 4.42(m, 1H); 3.90(s br, 1H); 3.50(dd, 1H); 3.20(d, 1H); 3.10(d, 1H); 3.09(d, 1H); 2.81(d, 1H); 2.69(m, 2H); 2.41(d, 1H); 2.31(d, 1H); 2.22–2.12(m, 1H); 1.91(s, 3H); 1.60(s br, 1H); 1.20(m, 1H); 1.20(d, 3H); 1.10(d, 3H) |

TABLE 2-continued

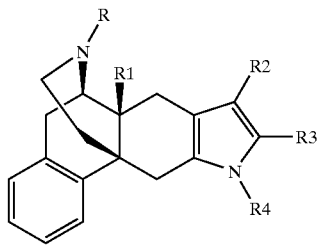

| Ex. | R | R1 | R2 | R3 | R4 | Synthesis | MP (° C.) (crystallization solvent) | MS m/z | MS conditions | NMR (δ ppm) |
|---|---|---|---|---|---|---|---|---|---|---|
| 3 | H | OH | Me | CON(Et)$_2$ | H | B | >240 (free base, acetone) | A) 394 (MH+) B) 321; 303; 260; 170 | A) ESI POS; TSQ 700; MeOH/spray 4.5 kV/skimmer: 60 V/capillary 220 C B) ESI DAU + 394 (Collision gas: Argon) | (CDCl3): 8.45(s br, 1H); 7.20(m, 1H); 7.09(m, 3H); 3.54(m, 2H); 3.49(dd, 1H); 3.39(m, 2H); 3.24(d, 1H); 3.17(d, 1H); 3.14(d, 1H); 2.88(d, 1H); 2.70(m, 2H); 2.42(d, 1H); 2.31(d, 1H); 2.22–2.12(m, 1H); 1.82(s, 3H); 1.75(s br, 2H); 1.22(m, 1H); 1.11(t, 6H). |
| 4 | H | H | Me | CON(iPr)CH$_2$Ph | H | B | 145–148 (free base, triturated with iPr$_2$O) | A) 454 (MH+) B) 454; 305; 276; 134 | A) ESI POS; TSQ 700; MeOH/spray 4.5 kV/skimmer: 60 V/capillary 220 C B) ESI DAU + 454 (Collision gas: Argon) | (CDCl3): 8.91(s br, 1H); 7.30–7.05(m, 9H); 4.58 and 4.50 (ABq, 2H); 4.40(m, 1H); 3.65(s br, 1H); 3.42(d, 1H); 3.37(dd, 1H); 3.11(m, 2H); 2.71(dt, 1H); 2.58(d, 1H); 2.28–2.15(m, 2H); 2.01(dt, 1H); 1.89(s, 3H); 1.86(m, 2H); 1.62(d, 1H); 1.20(d, 3H); 1.16(d, 3H). |
| 5 | H | OH | Me | CON(Et)CH$_2$Ph | H | B | 155–160 (free base, triturated with iPr$_2$O/iPrOH = 9/1) | A) 456 (MH+) B) 353; 335; 321; 303; 170 | A) ESI POS; TSQ 700; MeOH/spray 4.5 kV/skimmer: 60 V/capillary 220 C B) ESI DAU + 456 (Collision gas: Argon) | (CDCl3): 8.45(s br, 1H); 7.34–7.18(m, 6H); 7.08(m, 3H); 4.78(d, 1H); 4.52(d, 1H); 3.52(m, 1H); 3.49(dd, 1H); 3.29(m, 1H); 3.22(d, 1H); 3.14(d, 1H); 3.12(d, 1H); 2.87(d, 1H); 2.69(m, 2H); 2.41(d, 1H); 2.31(d, 1H); 2.22–2.12(m, 1H); 1.89(s, 3H); 1.70(s br, 2H); 1.22(m, 1H); 1.09(t, 3H). |
| 6 | H | OH | Me | 2-isoquinoline | H | C | >250 (free base, triturated with acetone) | A) 454 (MH+) B) 436; 335; 321; 303; 170 | A) ESI POS; TSQ 700; MeOH/spray 4.5 kV/skimmer: 60 V/capillary 220 C B) ESI DAU + 454 (Collision gas: Argon) | (DMSO, 373 K): 10.05(s br, 1H); 8.15(s, 1H); 7.28–7.00(m, 8H); 4.63 and 4.59(ABq, 2H); 3.70(t, 2H); 3.49(dd, 1H); 3.22(d, 1H); 3.21(d, 1H); 3.12(d, 1H); 2.90–2.69(m, 5H); 2.51(m, 1H); 2.38 and 2.31(ABq, 2H); 2.20(dt, 1H); 1.82(s, 3H); 1.15(d, 1H). |

TABLE 2-continued

| Ex. | R | R1 | R2 | R3 | R4 | Synthesis | MP (° C.) (crystallization solvent) | MS m/z | MS conditions | NMR (δ ppm) |
|---|---|---|---|---|---|---|---|---|---|---|
| 7 | H | OH | Me | COiBu | H | B | 170–175 (free base, triturated with Et$_2$O) | A) 379 (MH+) B) 379; 361; 344; 332; 277; 170 | A) ESI POS; TSQ 700; MeOH/spray 4.5 kV/skimmer: 60 V/capillary 220 C B) ESI DAU + 379 (Collision gas: Argon) | (CDCl3, 333 K): 9.30(s br, 1H); 7.10(m, 1H); 6.98(m, 3H); 3.42(dd, 1H); 3.22(d, 1H); 3.15(d, 1H); 3.11(d, 1H); 2.90(d, 1H); 2.67(m, 2H); 2.50–2.30(m, 4H); 2.20–2.10(m, 2H); 2.01(s, 3H); 1.75(s br, 2H); 1.20(d, 1H); 0.89(t, 6H). |
| 8 | H | OH | Me | CON(Et)Ph | H | B | >250 (.HCl, triturated with acetone) | A) 442 (MH+) B) 442; 424; 353; 321; 303; 170 | A) ESI POS; TSQ 700; MeOH/spray 4.5 kV/skimmer: 60 V/capillary 220 C B) ESI DAU + 442 (Collision gas: Argon) | (CDCl3, as base): 7.50(s br, 1H); 7.35–7.18(m, 3H); 7.12–7.00(m, 6H); 3.93(m, 2H); 3.45(dd, 1H); 3.15(d, 1H); 3.08(d, 1H); 2.87(d, 1H); 2.75(d, 1H); 2.65(m, 2H); 2.30(d, 1H); 2.19(d, 1H); 2.15–2.02(m, 1H); 1.62(s, 3H); 1.60(s br, 2H); 1.15(m, 1H); 1.15(t, 3H) |
| 9 | H | H | Me | CON(Et)Ph | H | B | 108–112 (free base, triturated with iPr$_2$O) | A) 440 (MH+); 305 B) 305; 288; 276; 260; 134 | A) ESI POS; TSQ 700; MeOH/spray 4.5 kV/skimmer: 60 V/capillary 220 C B) ESI DAU + 440 (Collision gas: Argon) | (CDCl3); 8.20(s br, 1H); 7.32–7.03(m, 9H); 4.71(d, 1H); 4.59(d, 1H); 3.51–3.27(m, 5H); 2.89(d, 1H); 2.80–2.60(m, 5H); 2.35(dd, 1H); 2.18(m, 1H); 1.97(m, 1H); 1.89(s, 3H); 1.78(dt, 1H); 1.56(m, 1H); 1.09(t, 3H). |
| 10 | H | OH | Me | CON(iPr)CH$_2$Ph | Me | B | (free base, amorphous solid) | A) 484 (MH+) B) 484; 466; 399; 297; 170; 91 | A) ESI POS; TSQ 700; MeOH/spray 4.5 kV/skimmer: 60 V/capillary 220 C B) ESI DAU + 484 (Collision gas: Argon) | (CDCl3, 338 K): 7.25–7.05(m, 9H); 4.64(d, 1H); 4.50–4.40(m, 2H); 3.50(dd, 1H); 3.45(s, 3H); 3.29(d, 1H); 3.20(d, 1H); 3.19(d, 1H); 2.74(m, 3H); 2.44(d, 1H); 2.30(d, 1H); 2.22–2.12(m, 1H); 1.80(s, 3H); 1.60(s br, 2H); 1.28(m, 1H); 1.19(d, 6H). |
| 11 | H | H | Me | CON(Et)CH$_2$Ph | Me | B | 110–112 (free base, triturated with iPr$_2$O) | A) 454 (MH+) B) 454; 425; 383; 319; 290; 283; 212; 192; 143; 91 | A) ESI POS; TSQ 700; MeOH/spray 4.5 kV/skimmer: 60 V/capillary 220 C B) ESI DAU + 454 (Collision gas: Argon) | (CDCl3, 343 K): 7.30–7.05(m, 9H); 4.68(d, 1H); 4.55(d, 1H); 3.49(s, 3H); 3.50–3.30(m, 5H); 2.98(d, 1H); 2.88–2.68(m, 2H); 2.52(d, 1H); 2.36(dd, 1H); 2.30–1.85(m, 4H); 1.80(s, 3H); 1.61(d, 1H); 1.08(t, 3H). |

TABLE 2-continued

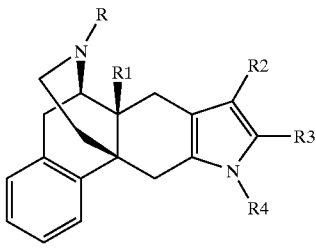

| Ex. | R | R1 | R2 | R3 | R4 | Synthesis | MP (° C.) (crystallization solvent) | MS m/z | MS conditions | NMR (δ ppm) |
|---|---|---|---|---|---|---|---|---|---|---|
| 12 | H | OH | Me | CO(cis-2,6-dimethylpiperidine) | H | B | >240 (free base, triturated with Et$_2$O) | A) 434 (MH+) B) 321; 303; 274; 260; 2476; 168 | A) ESI POS; TSQ 700; MeOH/spray 4.5 kV/skimmer: 60 V/capillary 220 C B) ESI DAU + 434 (Collision gas: Argon) | (CDCl3): 8.15(s br, 1H); 7.20(m, 1H); 7.08(m, 3H); 4.45–4.30(m, 2H); 3.90(s br, 1H); 3.50(dd, 1H); 3.20(d, 1H); 3.16(d, 1H); 3.11(d, 1H); 2.90(d, 1H); 2.69(m, 2H); 2.41(d, 1H); 2.31(d, 1H); 2.22–2.12(m, 1H); 1.90–1.50(m, 7H); 1.81(s, 3H); 1.22(d, 3H); 1.21(m, 1H); 1.20(d, 3H) |
| 13 | H | OMe | Me | CON(Et)CH$_2$Ph | H | B | 190–200 (free base, triturated with iPr$_2$O) | A) 484 (MH+) B) 484; 452; 367; 335; 303 | A) ESI POS; AQA; MeOH/spray 3 kV/ skimmer: 20 V/ probe 135 C B) CID Offset = 70 mV | (CDCl3): 8.49(s br, 1H); 7.22–7.05(m, 9H); 4.59 and 4.50(ABq, 2H); 4.39(m, 1H); 3.70(m, 1H); 3.39(m, 2H); 3.16(s, 3H); 3.11(d, 1H); 2.91(d, 1H); 3.85(dd, 1H); 2.65(dt, 1H); 2.60(d, 1H); 2.31(dt, 1H); 2.15(s br, 1H); 2.10(d, 1H); 1.92(s, 3H); 1.19(m, 1H); 1.19(d, 6H). |
| 14 | H | OH | Me | CON(iPr)CH$_2$PhpCF$_3$ | H | B | 160–165 (free base, triturated with iPr$_2$O) | A) 538 (MH+) B) 538; 520; 353; 335; 303 | A) ESI POS; AQA; MeOH/spray 3 kV/ skimmer: 20 V/ probe 135 C B) CID Offset = 70 mV | (CDCl3): 8.50(s br, 1H); 7.50(d, 2H); 7.38(d, 2H); 7.17–7.03(m, 4H); 4.69(d, 1H); 4.49(m, 1H); 4.45(d, 1H); 4.41(s br, 1H); 3.50(dd, 1H); 3.22(d, 1H); 3.12(d, 1H); 3.10(d, 1H); 2.77(d, 1H); 2.70(m, 2H); 2.40 and 2.31(ABq, 2H); 2.20–2.10(m, 1H); 1.95(s, 3H); 1.70(s br, 1H); 1.19(m, 1H); 1.19(d, 6H). |
| 15 | H | OH | Me | CON(iPr)CH$_2$PhmF | H | A | >250 (.HCl, triturated with Et$_2$O) | A) 488 (MH+) B) 488; 470; 393; 353; 335; | A) ESI POS; AQA; MeOH/spray 3 kV/ skimmer: 20 V/ probe 135 C B) CID Offset = 70 mV | (CDCl3): 8.70(s br, 1H); 7.25–6.99(m, 7H); 6.85(dt, 1H); 4.59 and 4.48(ABq, 2H); 4.43(m, 1H); 4.41(s br, 1H); 3.50(dd, 1H); 3.20(d, 1H); 3.10(d, 1H); 3.01(d, 1H); 2.75(d, 1H); 2.68(m, 2H); 2.40 and 2.30(ABq, 2H); 2.18–2.05(m, 1H); 1.92(s, 3H); 1.65(s br, 1H); 1.19(m, 1H); 1.19(d, 6H). |

TABLE 2-continued

| Ex. | R | R1 | R2 | R3 | R4 | Synthesis | MP (° C.) (crystallization solvent) | MS m/z | MS conditions | NMR (δ ppm) |
|---|---|---|---|---|---|---|---|---|---|---|
| 16 | H | OH | Me | CON(iPr)CH₂PhpBr | H | A | >250 (.HCl, triturated with Et₂O/acetone = 1/1) | A) 548 (MH+) B) 548; 353; 335; 321; 303 | A) ESI POS; AQA; MeOH/spray 3 kV/ skimmer: 20 V/ probe 135 C B) CID Offset = 70 mV | (CDCl3): 8.50(s br, 1H); 7.38(d, 2H); 7.17–7.03(m, 6H); 4.60(d, 1H); 4.41(m, 1H); 3.99(d, 1H); 3.98(s br, 1H); 3.50(dd, 1H); 3.20(d, 1H); 3.11(d, 1H); 3.09(d, 1H); 2.81(d, 1H); 2.69(m, 2H); 2.41 and 2.31(ABq, 2H); 2.20–2.09(m, 1H); 1.90(s, 3H); 1.70(s br, 1H); 1.20(m, 1H); 1.19(d, 3H) 1.18(d, 3H). |
| 17 | H | OH | Me | CON(iPr)CH₂Php(iPr) | H | B | 165–170 (free base, triturated with iPr₂O) | A) 511 (MH+) | A) ESI POS; AQA; MeOH/spray 3 kV/ skimmer: 20 V/ probe 135 C | |
| 18 | | OH | Me | CON(Cy)CH₂Ph | H | B | 170–165 (free base, triturated with iPr₂O) | A) 509 (MH+) | A) ESI POS; AQA; MeOH/spray 3 kV/ skimmer: 20 V/ probe 135 C | |
| 19 | Me | OH | Me | CON(iPr)2 | H | D | | | | |
| 20 | Me | OH | Me | CON(iPr)CH₂Ph | H | D | 238–240 (iPr₂O/acetone) | A) 484 (MH+); B) 484; 335; 317; 274; 218; 182. | A) ESI POS; TSQ 700; solvent: methanol/spray 4.5 kV/skimmer: 60 V/capillary 220° C.; B) ESI DAU + 480 (Collision gas: Argon) | (CDCl₃): 8.10(s br, 1H); 7.25–7.12(m, 6H); 7.08(m, 3H); 4.69(d, 1H); 4.42(d, 1H); 4.42(m, 1H); 3.30–2.90(m, 5H); 2.40(s, 3H); 2.50–2.30(m, 3H); 2.25–2.10(m, 2H); 1.91(s, 3H); 1.30–1.10(m, 7H). |
| 21 | Me | OH | Me | 2-isoquinoline | H | D | | | | |

What is claimed is:

1. A compound selected from:

[10R,4bR-(4b beta,9a beta)]-7-(N,N-diisopropyl)aminocarbonyl-8-methyl4b,5,9,9a, 10,11-hexahydro-9a-hydroxy-(6H)-10,4b-(iminoethano)phenanthro[3,2-b]pyrrole;

[10R,4bR-(4b beta,9a beta)]-7-[(N-benzyl-N-isopropyl)aminocarbonyl]-8-methyl-4b,5,9,9a,10,11-hexahydro-9a-hydroxy-(6H)-10,4b-(iminoethano)phenanthro-[3,2-b]pyrrole;

[10R,4bR-(4b beta,9a beta)]-7-(N,N-diethyl)aminocarbonyl-8-methyl-4b,5,9,9a,10,11-hexahydro-9a-hydroxy-(6H)-10,4b-(iminoethano)phenanthro[3,2-b]pyrrole;

[10R,4bS-(4b beta,9a beta)]-7-(N-isopropyl-N-benzyl)aminocarbonyl-8-methyl-4b,5,9,9a,10,11-hexahydro-(6H)-10-,4b-(iminoethano)phenanthro[3,2-b]pyrrole;

[10R,4bR-(4b beta,9a beta)]-7-(N-benzyl-N-ethyl)aminocarbonyl-8-methyl-4b,5,9,9a,10,11-hexahydro-9a-hydroxy-(6H)-10,4b-(iminoethano)phenanthro[3,2-b]pyrrole;

[10R,4bR-(4b beta,9a beta)]-7-( 1,2,3,4-tetrahydroisoquinolin-2-yl)carbonyl-8-methyl-4b,5,9,9a,10,11-hexahydro-9a-hydroxy-(6H)-10,4b-(iminoethano)phenanthro[3,2-b]pyrrole;

[10R,4bR-(4b beta,9a beta)]-7-isobutylcarbonyl-8-methyl-4b,5,9,9a, 10,11-hexahydro-9a-hydroxy-(6H)-10,4b-(iminoethano)phenanthro[3,2-b]pyrrole;

[10R,4bR-(4b beta,9a beta)]-7-[(N-phenyl-N-ethyl)aminocarbonyl]-4b,5,9,9a,10,11-hexahydro-9a-hydroxy-(6H)-8-methyl-10,4b-(iminoethano)-phenanthro[3,2-b]pyrrole;

[10R,4bS-(4b beta,9a beta)]-7-(N-ethyl-N-phenyl)aminocarbonyl-8-methyl-4b,5,9,9a,10,11-hexahydro-(6H)-10,4b-(iminoethano)phenanthro[3,2-b]pyrrole;

[10R,4bS-(4b beta,9a beta)]-7-(N-benzyl-N-isopropyl)
aminocarbonyl-6,8-dimethyl-4b,5,9,9a,10,11-
hexahydro-9a-hydroxy-(6H)-10,4b-(iminoethano)-
phenanthro[3,2-b]pyrrole;

[10R,4bS-(4b beta,9a beta)]-7-(N-ethyl-N-benzyl)
aminocarbonyl-6,8-dimethyl-4b,5,9,9a,10,11-
hexahydro-(6H)-10-,4b-(iminoethano)phenanthro[3,2-b]pyrrole;

[10R,4bR-(4b beta,9a beta)]-7-N-(cis-2,6-dimethyl)
piperidinylcarbonyl-4b,5,9,9a,10,11-hexahydro-9a-
hydroxy-(6H)-8-methyl-10,4b-(iminoethano)-
phenanthro[3,2-b]pyrrole;

[10R,4bR-(4b beta,9a beta)]-7-[(N-benzyl-N-ethyl)
aminocarbonyl]-4b,5,9,9a,10,11-hexahydro-9a-
methoxy-(6H)-8-methyl-10,4b-(iminoethano)-
phenanthro[3,2-b]pyrrole;

[10R,4bR-(4b beta,9a beta)]-7-[(N-(4-trifluoromethyl)
phenylmethyl-N-isopropyl)aminocarbonyl]-4b,5,9,9a,
10,11-hexahydro-9a-hydroxy-(6H)-8-methyl-10,4b-
(iminoethano)-phenanthro[3,2-b]pyrrole;

[10R,4bR-(4b beta,9a beta)]-7-[(N-(3-fluoro)
phenylmethyl-N-isopropyl)aminocarbonyl]-4b,5,9,9a,
10,11-hexahydro-9a-hydroxy-(6H)-8-methyl-10,4b-
(iminoethano)-phenanthro[3,2-b]pyrrole;

[10R,4bR-(4b beta,9a beta)]-7-[(N-(4-bromo)
phenylmethyl-N-isopropyl)aminocarbonyl]-4b,5,9,9a,
10,11-hexahydro-9a-hydroxy-(6H)-8-methyl-10,4b-
(iminoethano)-phenanthro[3,2-b]pyrrole;

[10R,4bR-(4b beta,9a beta)]-7-[(N-(4-isopropyl)
phenylmethyl-N-isopropyl)aminocarbonyl]-4b,5,9,9a,
10,11-hexahydro-9a-hydroxy-(6H)-8-methyl-10,4b-
(iminoethano)-phenanthro[3,2-b]pyrrole; and

[10R,4bR-(4b beta,9a beta)]-7-[(N-benzyl-N-cyclohexyl)
aminocarbonyl]-4b,5,9,9a,10,11-hexahydro-9a-
hydroxy-(6H)-8-methyl-10,4b-(iminoethano)-
phenanthro[3,2-b]pyrrole;

or a pharmaceutically acceptable salt or solvate of any one thereof.

2. [10R,4bR-(4b beta,9a beta)]-7-[(N-benzyl-N-isopropyl)aminocarbonyl]-8-methyl-4b,5,9,9a,10,11-hexahydro-9a-hydroxy-(6H)-10,4b-(iminoethano)phenanthro-[3,2-b]pyrrole or a pharmaceutically acceptable salt or solvate thereof.

3. A pharmaceutical composition comprising a compound according to claim 1, or a pharmaceutically acceptable salt or solvate thereof, and a pharmaceutically acceptable carrier.

4. A method of treating opioidergic network alteration or dysfunction comprising administering to a subject in need of treatment a safe and effective amount of a compound according to claim 1.

5. A method according to claim 4, wherein the compound administered is selected from the group consisting of an analgesic, an immunosuppressant to prevent rejection in organ transplant and skin graft, an anti-allergic agent, an anti-inflammatory agent, a brain cell protectant, an agent for treating drug and alcohol abuse, an agent for use in gastritis, or diarrhoea, an agent for use in cardiovascular and respiratory diseases, an agent for treating cough, an agent for treating mental illness or an agent for treating epilepsy.

* * * * *